United States Patent
Kim et al.

(10) Patent No.: US 8,098,382 B2
(45) Date of Patent: Jan. 17, 2012

(54) BEAM SCANNER AND SURFACE MEASUREMENT APPARATUS

(75) Inventors: Tak Gyum Kim, Gyunggi-do (KR); Bae Kyun Kim, Gyunggi-do (KR)

(73) Assignee: Samsung Electro-Mechanics Co., Ltd., Gyunggi-do (KR)

( * ) Notice: Subject to any disclaimer, the term of this patent is extended or adjusted under 35 U.S.C. 154(b) by 266 days.

(21) Appl. No.: 12/613,212

(22) Filed: Nov. 5, 2009

(65) Prior Publication Data

US 2010/0201993 A1 Aug. 12, 2010

(30) Foreign Application Priority Data

Feb. 6, 2009 (KR) .................. 10-2009-0009747

(51) Int. Cl.
*G01N 21/00* (2006.01)

(52) U.S. Cl. ...................................... 356/601; 356/614

(58) Field of Classification Search ........... 356/601–624
See application file for complete search history.

(56) References Cited

U.S. PATENT DOCUMENTS

| | | | | |
|---|---|---|---|---|
| 7,193,730 B2 * | 3/2007 | Higashi et al. | ................ | 356/615 |
| 2006/0092405 A1 * | 5/2006 | Higashi et al. | ................ | 356/127 |

FOREIGN PATENT DOCUMENTS

| | | |
|---|---|---|
| JP | 04-029005 | 1/1992 |
| JP | 11-005181 | 1/1999 |
| JP | 11-179579 | 7/1999 |
| KR | 10-2008-098811 | 11/2008 |

OTHER PUBLICATIONS

Korean Office Action, with English translation, issued in Korean Patent Application No. 10-2009-0009747, mailed Sep. 20, 2010.

* cited by examiner

*Primary Examiner* — Michael P Stafira

(74) *Attorney, Agent, or Firm* — McDermott Will & Emery LLP

(57) ABSTRACT

Disclosed are a beam scanner and a surface measurement apparatus. The beam scanner includes a spinning mirror having top and bottom reflective surfaces and a plurality of side reflective surfaces between the top and bottom reflective surfaces, and rotating about a rotary shaft penetrating the top and bottom reflective surfaces to scan beams, falling onto the side reflective surface, in one direction, a first light source emitting first beams to the side reflective surface, a second light source emitting second beams to at least one of the top and bottom reflective surfaces, and a detector receiving beams reflected by the spinning mirror, among the second beams. The beam scanner and the surface measurement apparatus can achieve high-speed, high resolution surface measurement since errors caused by the movement of the spinning mirror for beam scanning are minimized.

10 Claims, 3 Drawing Sheets

BEAM SCANNER AND SURFACE MEASUREMENT APPARATUS

CROSS-REFERENCE TO RELATED APPLICATIONS

This application claims the priority of Korean Patent Application No. 10-2009-0009747 filed on Feb. 6, 2009, in the Korean Intellectual Property Office, the disclosure of which is incorporated herein by reference.

BACKGROUND OF THE INVENTION

1. Field of the Invention

The present invention relates to a beam scanner and a surface measurement apparatus, and more particularly, to abeam scanner and a surface measurement apparatus which can minimize errors caused by the movement of a spinning mirror for beam scanning.

2. Description of the Related Art

In general, semiconductor integrated circuits are fabricated by forming circuits on a wafer using a photolithography process. In this case, a plurality of the same integrated circuits are disposed on a wafer and divided into individual integrated circuit chips. If foreign bodies exist on the wafer, defective circuit patterns may be formed in the wafer portion where the foreign bodies exist. This may render the use of a corresponding integrated circuit impossible. As a result, integrated circuits obtainable from a single wafer decrease in number, and the yield is reduced. In addition to the semiconductor integrated circuits, examples of advanced materials that are adversely affected by foreign bodies or defects on the micrometer scale may include glass for display devices and materials for circuit boards. Accordingly, there is a need for equipment for measuring and inspecting such foreign bodies or defects.

In general, a method of collecting lasers on the surface of a wafer, receiving light scattered from a laser collection point on the wafer and detecting foreign bodies based on a signal corresponding to the received light is in use, to measure foreign bodies or defects on a wafer.

FIG. 1 is a schematic perspective view depicting a related art surface measurement apparatus.

Referring to FIG. 1, a related art surface measurement apparatus 10 includes a light source emitting laser beams (L), an object 11 of measurement, such as a wafer, and first and second beam detectors 12 and 13. The first beam detector 12 detects beams Ls scattered from the wafer 11. That is, light, scattered from a light collection point on the wafer 11, is collected in the first beam detector 12 serving as a photoelectric converter, through a lens. The first beam detector 12, having collected the scattered light, outputs a pulse signal corresponding to the intensity of beams scattered by foreign bodies. Thus, the sizes of the foreign bodies may be determined based on the magnitude of the output signal. The second beam detector 13 detects a beam Lr reflected by the wafer 11. By detecting signals by both scattered and reflected beams, the surface measurement apparatus 10 can determine the presence of foreign bodies on the wafer 11, measure the sizes of the foreign bodies and also measure the angle of the reflected beam to obtain a three-dimensional shape.

SUMMARY OF THE INVENTION

An aspect of the present invention provides a beam scanner and a surface measurement apparatus, capable of high-speed, high resolution surface measurement by minimizing an error caused by the movement of a spinning mirror for beam scanning.

According to an aspect of the present invention, there is provided a beam scanner including: a spinning mirror having top and bottom reflective surfaces and a plurality of side reflective surfaces between the top and bottom reflective surfaces, and rotating about a rotary shaft penetrating the top and bottom reflective surfaces to scan beams, falling onto the side reflective surface, in one direction; a first light source emitting first beams to the side reflective surface; a second light source emitting second beams to at least one of the top and bottom reflective surfaces; and a detector receiving beams reflected by the spinning mirror, among the second beams.

The spinning mirror may be a polygon mirror.

The detector may serve as a corrector that corrects a scanning position of the first beam according to a vertical movement of the polygon mirror.

The detector may be a quadruple position sensitive detector.

According to another aspect of the present invention, there is provided a surface measurement apparatus including: a stage receiving an object of measurement; a spinning mirror having top and bottom reflective surfaces and a plurality of side reflective surfaces between the top and bottom reflective surfaces, and rotating about a rotary shaft penetrating the top and bottom reflective surfaces to scan beams, falling onto the side reflective surface, in one direction; a first light source emitting first beams to the side reflective surface; a second light source emitting second beams to at least one of the top and bottom reflective surfaces; a first detector receiving beams reflected by the object of measurement, among the first beams scanned by the spinning mirror; and a second detector receiving beams reflected by the spinning mirror, among the second beams.

The first detector may include a position-signal detection part and a reflection-amount detection part.

The second detector may serves as a corrector that corrects a scanning position of the first beams according to a vertical movement of the polygon mirror. Signals received in the first and second detectors are synchronized with each other.

BRIEF DESCRIPTION OF THE DRAWINGS

The above and other aspects, features and other advantages of the present invention will be more clearly understood from the following detailed description taken in conjunction with the accompanying drawings, in which.

DETAILED DESCRIPTION OF THE PREFERRED EMBODIMENT

Figure 1:
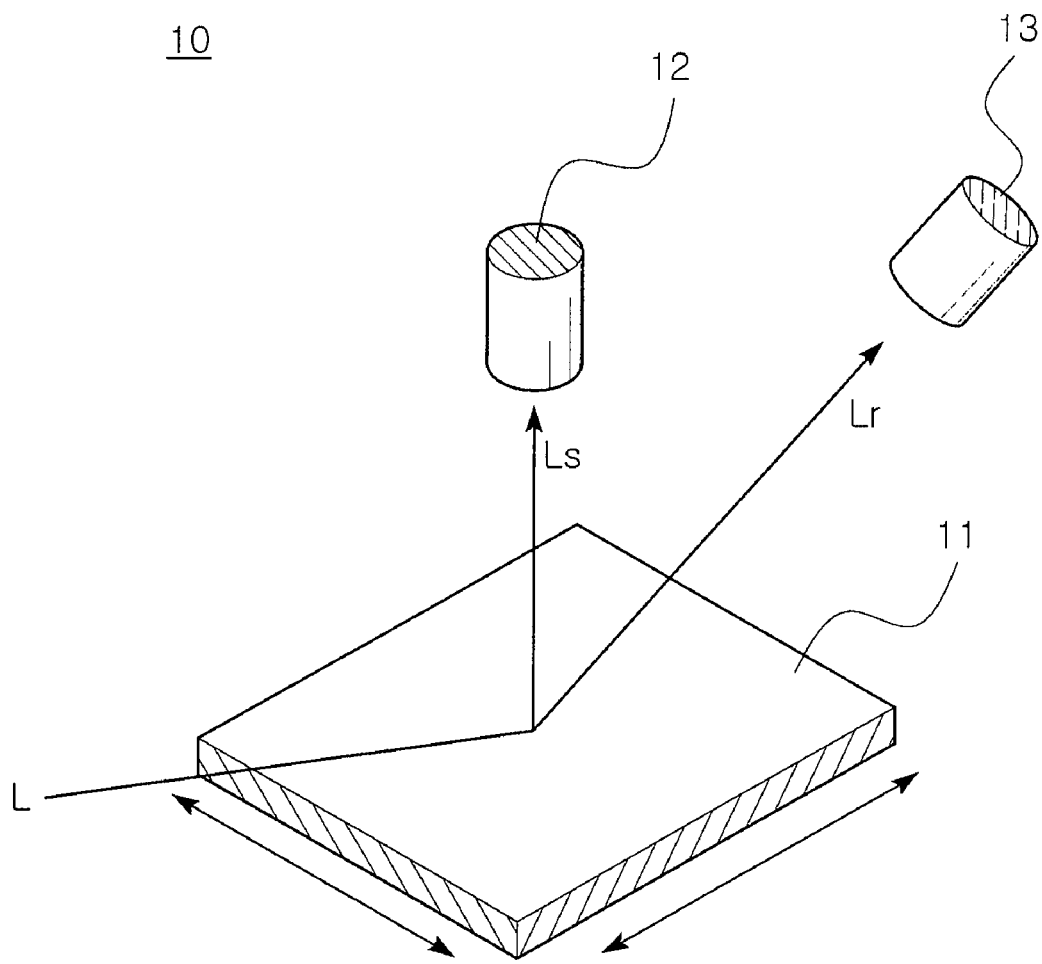
FIG. 1 is a schematic perspective view depicting a related art surface measurement apparatus.

Exemplary embodiments of the present invention will now be described in detail with reference to the accompanying drawings.

The invention may, however, be embodied in many different forms and should not be construed as limited to the embodiments set forth herein. Rather, these embodiments are provided so that this disclosure will be thorough and complete, and will fully convey the scope of the invention to those skilled in the art. In the drawings, the shape and dimension of elements may be exaggerated for clarity. Like reference numerals in the drawings denote like elements.

Figure 2:
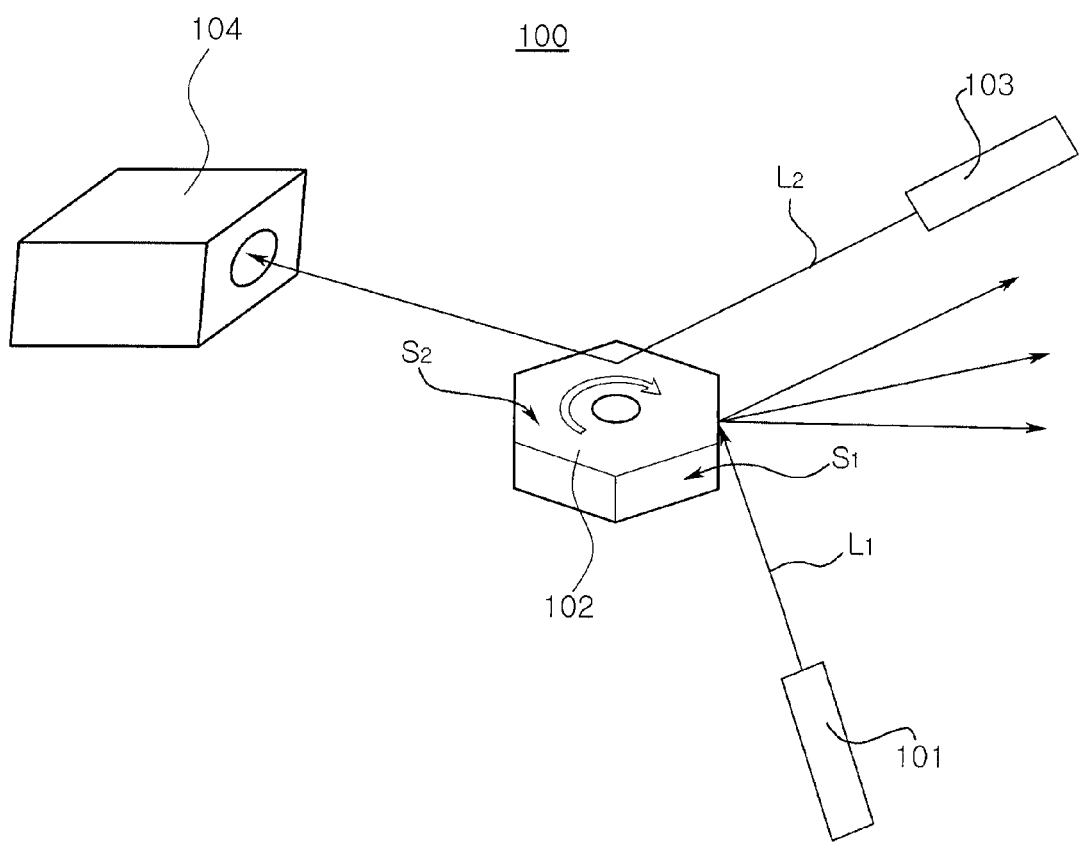
FIG. 2 is a perspective view depicting a beam scanner according to an exemplary embodiment of the present invention.

FIG. 2 is a perspective view depicting a beam scanner according to an exemplary embodiment of the present invention. Referring to FIG. 2, a beam scanner 100, according to this embodiment, includes a first light source 101, a spinning mirror 102, a second light source 103, and a detector 104.

The first light source 101 emits first beams L1 to a reflective surface S1 (hereinafter, referred to as 'side reflective surface') which is placed at the side portion of the spinning mirror 102. Here, the rotation of the spinning mirror 102 allows the first beam L1 to be scanned in one direction. The first beam L1, scanned in this manner, may be used to detect foreign bodies on a wafer or the like, as will be described later. In order to measure the surface state of an object of measurement such as a wafer, the first light source 101 emits beams, for example, laser beams, which can be reflected and scattered by the object of measurement.

The spinning mirror 102 has top and bottom reflective surfaces, and the side reflective surface S1 is placed between the top and bottom reflective surfaces. As for the spinning mirror 102, a polygon mirror may be used as shown in FIG. 2. Besides the polygon mirror, the spinning mirror 102 may also utilize a Galvano mirror or a cylindrical mirror, for example. However, the polygon mirror may be used to reduce expenses.

As described above, the spinning mirror 102 rotates about a rotary shaft penetrating the top and bottom reflective surfaces to thus scan the first beam L1 in one direction, however, this rotation may cause undesired movements. In particular, when the polygon mirror is used as in this embodiment, the spinning mirror 102 may wobble in a vertical direction. Here, an example of this vertical wobbling may include the regular or irregular vibration of the spinning mirror 102 in the direction of the rotary shaft. As compared to the movement perpendicular to this vertical wobbling, that is, the horizontal movement thereof, the vertical wobbling of the spinning mirror 102 has significant influence on the direction in which the first beam L1 is scanned, and this may bring about errors in measuring the position and size of foreign bodies.

In order to prevent limitations caused by the vertical wobbling, this embodiment employs the second light source 103 emitting second beams L2 to the top reflective surface S2 of the spinning mirror 102, and the detector 104 receiving beams reflected by the top reflective surface S2 among the second beams L2. Although beams are emitted only onto the top reflective surface S2 of the spinning mirror 102 in FIG. 2, beams may be emitted only onto the bottom reflective surface or onto both the top and bottom reflective surfaces to thereby further enhance precision.

Figure 3:
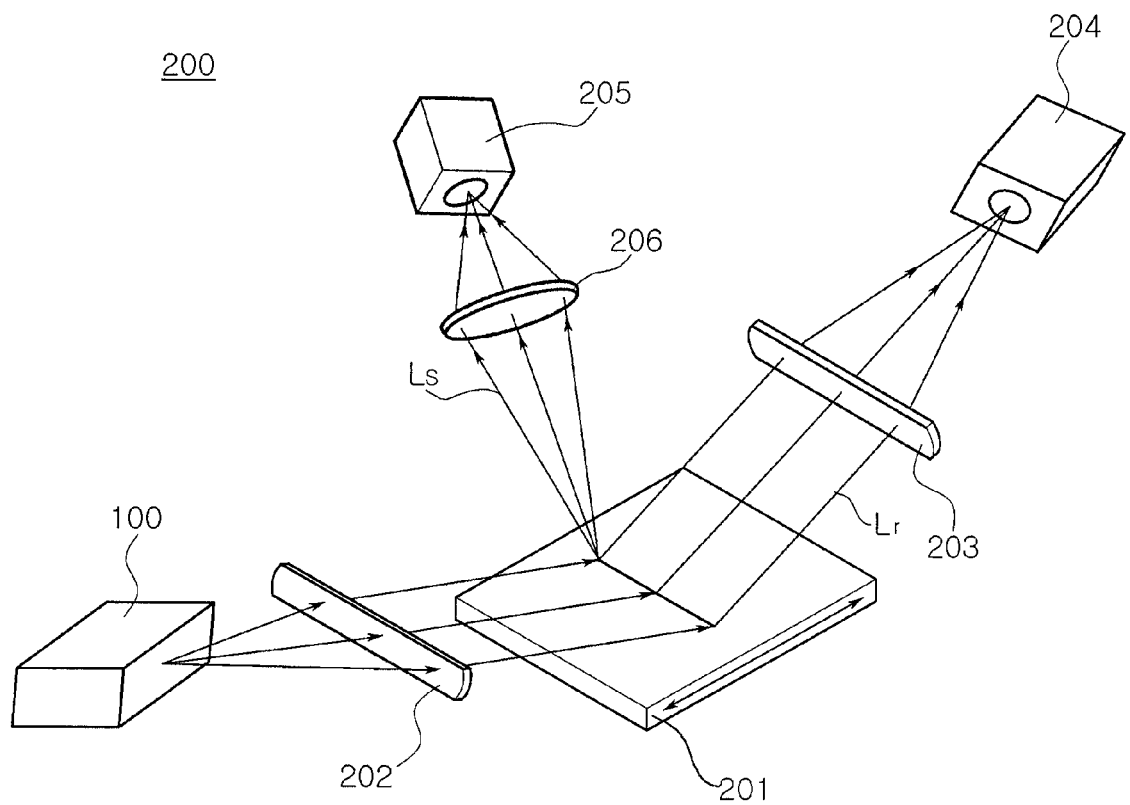
FIG. 3 is a perspective view depicting a surface measurement apparatus according to an exemplary embodiment of the present invention.

The second light source 103 may utilize the same light source as the first light source 101, and the detector 104 measures positional information associated with wobbling during the high-speed rotation of the spinning mirror 102. To this end, the detector 104 may utilize a quadruple position sensitive detector (QPSD) so as to measure positional information regarding multiple axes. When the beam scanner 100 is used in a surface measurement apparatus as shown in FIG. 3, a signal measured by the detector 104 is synchronized on the temporal axis with the signal of the first beams L1 reflected by the object of measurement, or beams scattered by it. Thus, information can be provided that serves to accurately detect the position of foreign bodies on the surface of the object of measurement.

As described above, the beam scanner 100, according to this embodiment, corrects the wobbling of the spinning mirror 102 and is thus applicable to a high-precision surface measurement apparatus. Also, the beam scanner 100 may serve to achieve high-speed, high resolution surface measurements, using the relatively low-priced polygon mirror.

FIG. 3 is a perspective view depicting a surface measurement apparatus according to an exemplary embodiment of the present invention. Referring to FIG. 3, a surface measurement apparatus 200, according to this embodiment, includes a beam scanner 100, a stage 201, first and second lenses 202 and 203, a reflected-beam detector 204, and a scattered-beam detector 205.

The beam scanner 100, although not shown in FIG. 3 in detail, may have a structure depicted in FIG. 2. That is, beams scanned from the beam scanner 100 correspond to the first beams L1 in FIG. 2.

The stage 201 receives an object (not shown) of measurement, such as a wafer, on the top thereof, and moves the object of measurement linearly. This linear movement and the one-direction scanning of the beam scanner 100 allow the entire surface of the object of measurement to be measured without moving the beam scanner 100.

A scanning beam from the beam scanner 100 is emitted to the object of measurement on the stage 201 via the first lens 202, and beams Lr reflected by the object of measurement are received in the reflected-beam detector 204 via the second lens 203. As for the first and second lenses 202 and 203, f-θ lenses may be used. Beams Ls scattered by the object of measurement may be received in the scattered-beam detector 205 placed above the object of measurement, via a condenser lens 206.

The reflected-beam detector 204 and the scattered-beam detector 205 are devices that can convert optical signals into electrical signals and analyze the converted signals. The scattered-beam detector 205 is disposed above the object of measurement, and converts an optical signal into a current signal and interprets this current signal, thereby determining the position, or the like, of the object of measurement. Also, the scattered-beam detector 205 may be used to correct the output of the reflected-beam detector 204. That is, the scattered-beam detector 205 serves to detect beams scattered by the object of measurement, that is, a noise signal, which is irregularly reflected by foreign bodies or the like existing on the surface thereof. If there are no foreign bodies or cracks in the surface of the object of measurement, most beams being scanned over the surface of the object of measurement are not scattered but reflected and received in the reflected-beam detector 204. However, if foreign bodies or the like exist thereon, the intensity of the scattered beam Ls increases instantly. The scattered beams and the reflected beams are analyzed together, so that the positions or sizes of foreign bodies can be determined.

In the process of detecting foreign bodies, the detector 104, measuring the vertical wobbling of the spinning mirror 102 included in the beam scanner 100, is synchronized with the reflected-beam detector 204. The positions and shapes of foreign bodies may be corrected more precisely based on information associated with the wobbling of the spinning mirror 102 provided by the detector 104. Accordingly, the surface measurement apparatus 200, according to this embodiment, may achieve high resolution in the level of 1 μm, despite the high-speed wobbling of the polygon mirror.

The reflected-beam detector 204 may include a reflection amount measuring part and a position-signal detection part (PSD), so that a three-dimensional shape can be measured. That is, the position-signal detection part can measure the changes in the angle of reflected beams, and thus a three-dimensional shape can be measured based on the measured values by using a triangulation method. Accordingly, a three-dimensional shape may be measured according to morphological changes.

As set forth above, according to exemplary embodiments of the invention, errors caused by the movement of the spinning mirror for beam scanning are minimized, so that the beam scanner and the surface measurement apparatus can achieve high-speed, high resolution surface measurements. Particularly, according to the present invention, surface measurements can be performed with high precision, using the relatively low-priced polygon mirror.

While the present invention has been shown and described in connection with the exemplary embodiments, it will be apparent to those skilled in the art that modifications and variations can be made without departing from the spirit and scope of the invention as defined by the appended claims.

What is claimed is:

1. A beam scanner comprising:
   a spinning mirror having top and bottom reflective surfaces and a plurality of side reflective surfaces between the top and bottom reflective surfaces, and rotating about a rotary shaft penetrating the top and bottom reflective surfaces to scan beams, falling onto the side reflective surface, in one direction;
   a first light source emitting first beams to the side reflective surface;
   a second light source emitting second beams to at least one of the top and bottom reflective surfaces; and
   a detector receiving beams reflected by the spinning mirror, among the second beams.

2. The beam scanner of claim 1, wherein the spinning mirror is a polygon mirror.

3. The beam scanner of claim 1, wherein the detector serves as a corrector that corrects a scanning position of the first beam according to a vertical movement of the polygon mirror.

4. The beam scanner of claim 1, wherein the detector is a quadruple position sensitive detector.

5. A surface measurement apparatus comprising:
   a stage receiving an object of measurement;
   a spinning mirror having top and bottom reflective surfaces and a plurality of side reflective surfaces between the top and bottom reflective surfaces, and rotating about a rotary shaft penetrating the top and bottom reflective surfaces to scan beams, falling onto the side reflective surface, in one direction;
   a first light source emitting first beams to the side reflective surface;
   a second light source emitting second beams to at least one of the top and bottom reflective surfaces;
   a first detector receiving beams reflected by the object of measurement, among the first beams scanned by the spinning mirror; and
   a second detector receiving beams reflected by the spinning mirror, among the second beams.

6. The surface measurement apparatus of claim 5, wherein the spinning mirror is a polygon mirror.

7. The surface measurement apparatus of claim 5, wherein the first detector includes a position-signal detection part and a reflection-amount detection part.

8. The surface measurement apparatus of claim 5, wherein the second detector serves as a corrector that corrects a scanning position of the first beams according to a vertical movement of the polygon mirror.

9. The surface measurement apparatus of claim 5, wherein the second detector is a quadruple position sensitive detector.

10. The surface measurement apparatus of claim 5, wherein signals received in the first and second detectors are synchronized with each other.

* * * * *